(12) United States Patent
Mareiniss (10) Patent No.: US 11,433,206 B2
(45) Date of Patent: Sep. 6, 2022

(54) RESPIRATORY TREATMENT ISOLATION HOOD

(71) Applicant: Darren Peter Mareiniss, Rydal, PA (US)

(72) Inventor: Darren Peter Mareiniss, Rydal, PA (US)

( * ) Notice: Subject to any disclaimer, the term of this patent is extended or adjusted under 35 U.S.C. 154(b) by 0 days.

(21) Appl. No.: 17/340,656

(22) Filed: Jun. 7, 2021

(65) Prior Publication Data

US 2022/0001126 A1 Jan. 6, 2022

Related U.S. Application Data

(60) Provisional application No. 63/048,190, filed on Jul. 5, 2020.

(51) Int. Cl.
*A61M 16/06* (2006.01)
*A61M 16/10* (2006.01)

(52) U.S. Cl.
CPC .... *A61M 16/0627* (2014.02); *A61M 16/0672* (2014.02); *A61M 16/107* (2014.02); *A61M 16/1055* (2013.01); *A61M 16/1065* (2014.02); *A61M 2205/7509* (2013.01); *A61M 2205/7518* (2013.01)

(58) Field of Classification Search
CPC ............ A41D 13/0005; A41D 2300/30; A61G 10/005; A61G 10/04; A61G 13/1215; A61G 2210/00; A61M 16/00; A61M 16/009; A61M 16/01; A61M 16/0409; A61M 16/06; A61M 16/0627; A61M 16/107; A61M 16/208; A61M 2202/0208; A61M 2202/0241; A61M 2205/0216; A61M 2205/053; A62B 17/04; A62B 18/04; A62B 18/10; A62B 7/00; B63C 11/06

See application file for complete search history.

(56) References Cited

U.S. PATENT DOCUMENTS

| | | | | |
|---|---|---|---|---|
| 3,739,774 A | * | 6/1973 | Gregory | A62B 18/04 128/201.28 |
| 3,889,670 A | * | 6/1975 | Loveland | A61G 10/04 128/203.12 |
| 3,958,275 A | * | 5/1976 | Morgan | B63C 11/06 2/421 |
| 5,690,095 A | * | 11/1997 | Glynn | A62B 17/04 128/201.23 |

(Continued)

*Primary Examiner* — Annette Dixon (57) ABSTRACT

An isolation hood for respiratory treatment is disclosed. The isolation hood may include a head enclosure defining an interior volume configured to receive the head of a patient, and a neck seal configured to couple the head enclosure to a neck of the patient. The isolation hood may include an inlet port configured to be coupled to a distal end of a treatment source tube and to a first end of a treatment delivery tube, and an outlet port configured to be coupled to an inline particle filter configured to permit air to flow through the head enclosure. The neck seal and the inline particle filter are each configured to prevent viral/bacterial aerosolization outside the hood. The inlet and outlet ports may be attached to respiratory tubing and non-invasive ventilatory equipment to permit aerosol-generating procedures within the hood while preventing viral/bacterial aerosolization outside the hood.

19 Claims, 6 Drawing Sheets

(56) References Cited

U.S. PATENT DOCUMENTS

| | | | | |
|---|---|---|---|---|
| 6,102,034 | A * | 8/2000 | Buhlmann | A62B 17/04 128/201.13 |
| 6,701,920 | B1 * | 3/2004 | Cox | A62B 17/04 128/201.22 |
| 6,854,459 | B1 * | 2/2005 | Cox | A62B 17/04 128/201.22 |
| 9,931,482 | B2 * | 4/2018 | Ritchie | A61M 16/06 |
| 10,799,727 | B2 * | 10/2020 | Giulianotti | A61M 16/0627 |
| 2006/0137686 | A1 * | 6/2006 | Macris | A61M 16/06 128/201.22 |
| 2014/0331999 | A1 * | 11/2014 | Rossi | A61M 16/0627 128/202.27 |
| 2021/0315758 | A1 * | 10/2021 | Bui | A61M 16/01 |

\* cited by examiner

210 — Place neck seal assembly over the user's head

220 — Install a mask or nasal cannula onto the user's head

230 — Bring the head enclosure close to the neck seal assembly

240 — Attach the connection ports to the treatment source tube and any other tubes 250 — Mate the head enclosure with the neck seal assembly by inserting the neck seal assembly into the lower socket of the head enclosure 260 — Attach partuclate filter to outer end of the outlet port 270 — After use, separate head enclosure from neck sesal and disconnect mask/cannula from patient 280 — Sanitize isolation hood and replace flexible septum

FIG. 5 ly important in general and particularly during an infectious disease pandemic in which viral pneumonia and hypoxia are common. Currently, the COVID-19 pandemic has created a situation in which most hospitals are avoiding aerosol-generating procedures to protect the staff and to prevent transmission of this deadly disease. Many patients present to the hospital with hypoxia, hypercarbia, and other respiratory complaints, and they require such aerosol-generating procedures to avoid intubation and/or to treat their respiratory complaints. Aerosol-generating procedures include nebulizer treatments, CPAP, BiPAP, and high flow nasal cannula.

RESPIRATORY TREATMENT ISOLATION HOOD

CROSS-REFERENCE TO RELATED APPLICATIONS

This application claims the benefit of the filing date of U.S. Provisional Patent Application No. 63/048,190, filed Jul. 5, 2020, the disclosure of which is hereby incorporated herein by reference.

BACKGROUND OF THE INVENTION

The use of non-invasive ventilatory strategies, such as high flow nasal cannula oxygen, bilevel positive airway pressure ventilation (BiPAP) and continuous positive airway pressure ventilation (CPAP), is critically important in general and particularly during an infectious disease pandemic in which viral pneumonia and hypoxia are common. Currently, the COVID-19 pandemic has created a situation in which most hospitals are avoiding aerosol-generating procedures to protect the staff and to prevent transmission of this deadly disease. Many patients present to the hospital with hypoxia, hypercarbia, and other respiratory complaints, and they require such aerosol-generating procedures to avoid intubation and/or to treat their respiratory complaints. Aerosol-generating procedures include nebulizer treatments, CPAP, BiPAP, and high flow nasal cannula.

Aerosol-generating procedures that were normally performed in standard hospital rooms, many of which are life-saving procedures, have been avoided or only performed in specialized negative pressure rooms to avoid aerosolizing the virus and potentially spreading it to staff and other patients. These procedures include nebulizer medication treatments (e.g., albuterol, Atrovent, and epinephrine), BiPAP non-invasive ventilation, CPAP non-invasive ventilation, nasal cannula treatment, and high flow nasal cannula treatment. However, hospitals do not have many negative pressure rooms. These rooms are both expensive and time-consuming to build. There is a need for a safe way to perform non-invasive ventilation (BiPAP, CPAP, and high flow nasal cannula) and other aerosol-generating procedures (e.g., nebulizer treatments) outside of negative pressure rooms, while avoiding aerosolization of infectious viruses/bacteria into the surrounding environment.

BRIEF SUMMARY OF THE INVENTION

An isolation hood for respiratory treatment may include a head enclosure defining an interior volume therein and configured to receive the head of a patient within the interior volume, the head enclosure having an opening at a bottom thereof, the opening configured to receive the neck of a patent therein. The isolation hood may also include a neck seal disposed at the opening, the neck seal configured to couple the head enclosure to the neck of the patient, the neck seal configured to prevent aerosolized viral or bacterial particles from flowing from the interior volume to an ambient environment outside of the head enclosure.

The isolation hood may also include an inlet port extending through the head enclosure, an outer end of the inlet port outside the head enclosure configured to be coupled to a distal end of a treatment source tube, an inner end of the inlet port inside the head enclosure configured to be coupled to a first end of a treatment delivery tube of a mask or a nasal cannula placed on the patient. The isolation hood may also include an outlet port extending through the head enclosure, an outer end of the outlet port outside of the head enclosure configured to be coupled to an inline particle filter, the inline particle filter configured to prevent the aerosolized viral or bacterial particles from flowing from the interior volume to the ambient environment outside of the head enclosure. The inlet port may be configured to connect to a non-invasive aerosol-generating treatment within the interior volume, the non-invasive aerosol-generating treatment including: bilevel positive airway pressure ventilation, continuous positive airway pressure ventilation, nebulizer treatments, oxygen cannula, mask, or high-flow nasal cannula treatments to the patient.

The inlet port may be a first inlet port, the isolation hood further including a second inlet port extending through the head enclosure and configured to be coupled to the non-invasive aerosol-generating treatment or an input of one or more of air, gas, or oxygen. The neck seal may include a neck ring that is configured to be removably coupled to an inner edge of the head enclosure at the opening, the neck seal having an outer periphery attached to the neck ring and an inner aperture remote from the outer periphery. The neck seal may include a durable elastic material. The isolation hood may also include the inline particle filter coupled to the outer end of the outlet port. The isolation hood may also include an inline positive end expiratory pressure valve coupled to the inline particle filter or the outer end of the outlet port and configured to maintain the interior volume above atmospheric pressure. The neck seal may include a hook and loop closure configured to fasten the neck seal around the neck of the patient.

The isolation hood may also include a pressure port, an outer end of the pressure port outside the head enclosure configured to be coupled to a distal end of a suction tube, the suction tube configured to remove gas from the interior volume within the head enclosure to maintain the interior volume below atmospheric pressure. The isolation hood may also include a viral filter in line with the suction tube. The isolation hood may also include a pressure port and an inline positive end expiratory pressure valve, an outer end of the pressure port outside the head enclosure configured to be coupled to a distal end of a high-pressure tube, the high-pressure tube configured to supply a pressurized gas into the interior volume within the head enclosure to maintain the interior volume above atmospheric pressure, the inline positive end expiratory pressure valve coupled to the pressure port or the outer end of the outlet port and configured to maintain the interior volume above atmospheric pressure.

The isolation hood may also include the treatment delivery tube, a first end of the treatment delivery tube coupled to the inner end of the inlet port, a second end of the treatment delivery tube configured to be coupled to the mask or the nasal cannula. The isolation hood may also include the mask, and the mask may be a nebulizer treatment mask. The isolation hood may also include the mask, and the mask may be a continuous positive airway pressure system mask or a bilevel positive airway pressure system mask. The isolation hood may also include the nasal cannula, and the nasal cannula may be a high flow nasal cannula. The inlet port may be configured to provide a gas flow to washout excess $CO_2$ from the interior volume of the isolation hood. The gas flow may be provided at a flow rate that is sufficient to prevent hypercarbia.

A kit may include the isolation hood described above and an alternate neck seal. The neck seal and the alternate neck seal may have inner apertures having different diameters, the neck seal and the alternate neck seal each configured to be removably coupled to an inner edge of the head enclosure at the opening.

A method of using an isolation hood for respiratory treatment may include placing the isolation hood around a head and neck of a patient, the isolation hood having a head enclosure defining an interior volume in which the head of the patient is received, the head enclosure having an opening at a bottom thereof extending around the neck of the patent, the isolation hood having a neck seal at the opening coupling the head enclosure to the neck of the patient, the isolation hood having an inlet port and an outlet port each extending through the head enclosure, an outer end of the inlet port coupled to a distal end of a treatment source tube, an outer end of the outlet port coupled to an inline particle filter, an inner end of the inlet port coupled to a first end of a treatment delivery tube.

The method may also include coupling a second end of the treatment delivery tube to the head of the patient. The method may also include flowing a medicine in a carrier gas through the treatment source tube and through the delivery treatment tube. The neck seal and the inline particle filter may together prevent the aerosolized viral or bacterial particles from flowing from the interior volume to the ambient environment outside of the head enclosure.

The method may also include suctioning gas out of the interior volume through a pressure port extending through the head enclosure, the suctioning maintaining the interior volume below atmospheric pressure. The method may also include flowing a pressurized gas into the interior volume through a pressure port extending through the head enclosure, the pressurized gas maintaining the interior volume above atmospheric pressure using at least one of: a pressure valve or a positive end expiratory pressure valve inline on the outlet port. The second end of the treatment delivery tube may include a nebulizer treatment mask, and the medicine may be a nebulizer treatment compound. The second end of the treatment delivery tube may include a continuous positive airway pressure system mask or bilevel positive airway pressure system mask. The second end of the treatment delivery tube may include a facemask. The second end of the treatment delivery tube may include a nasal cannula.

DETAILED DESCRIPTION

This invention relates to a hood tent for covering a person's head and allowing aerosol-generating respiratory treatments and interventions to be performed without the risk of contaminating the surrounding environment with viral or bacterial particles.

To allow non-invasive aerosolizing procedures without a negative pressure room, the invention creates a sealed hood around a patient's head or head and neck. The invention allows for several different non-invasive respiratory therapies to connect to the hood and connect from the hood to the patient. The hood air outlet allows for an adapter that can be connected to a viral/bacterial filter to filter all the air coming from the hood to the surrounding environment. Although particles are aerosolized within the hood by the non-invasive ventilation or respiratory treatments being performed therein, the invention can prevent viral/bacterial particles from spreading to the ambient environment by use of a filter at the outflow port.

This invention allows for the inflow and outflow of oxygen at different levels of concentration and pressure. The isolation hood may maintain an elevated pressure through the use of positive end expiratory pressure valves on the outflow. This may by connected in series with a viral and/or bacterial filter to prevent aerosolized virus or bacteria from leaving the hood into the surrounding environment.

There have been various hoods described in the prior art that can be placed on a person's head. However, none of these prior inventions teach or allow for the use of aerosolizing treatments or equipment within the hood, nor do they provide adapters for such equipment to be connected within the hood to the face of a patient. Use of the present invention will allow many more patients to be treated in hospitals without needing a negative pressure room. It will allow patients to receive non-invasive ventilation and aerosolizing procedures without the risk of aerosolization of virus and bacteria outside of the hood. In some embodiments, an infusion of gas into the isolation hood can be implemented to create a positive pressure environment for oxygenating a patient.

This disclosure describes a large isolation hood that affixes and/or seals to a neck ring piece which includes a flexible sized neck seal that fits around a person's neck. The isolation hood may include at least two ports on the exterior of the hood or neck ring that connect through to ports within the hood. The hood is partially transparent and large enough to provide space for respiratory treatments and equipment including nebulizer treatments, nasal cannula, high flow nasal cannula, continuous positive pressure ventilation systems, bilevel positive airway pressure ventilation, respiratory masks, treatments and equipment. The hood may be connected to a ventilator or oxygen source to allow for non-invasive ventilation. The outlet may be connected to an inline filter and PEEP valve (positive end-expiratory pressure) to maintain elevated pressures with the helmet and to provide continuous positive airway pressure to assist the patient in oxygenation. The isolation hood may be used as an oxygen tent or in conjunction with oxygen under pressure. The isolation hood may be used for pressure support, continuous positive airway pressure without the addition of another device. The isolation hood may be used for noninvasive ventilation and oxygenation.

As used herein, the terms "proximal" and "distal" are to be taken as relative to a user of the various hoods that are described. "Proximal" is to be understood as relatively close to the user, and "distal" is to be understood as relatively farther away from the user. Furthermore, as used herein, the terms "generally," "substantially," "approximately," and "about" are to be understood to mean that slight deviations from absolute are included within the scope of the term so modified.

Figure 1:
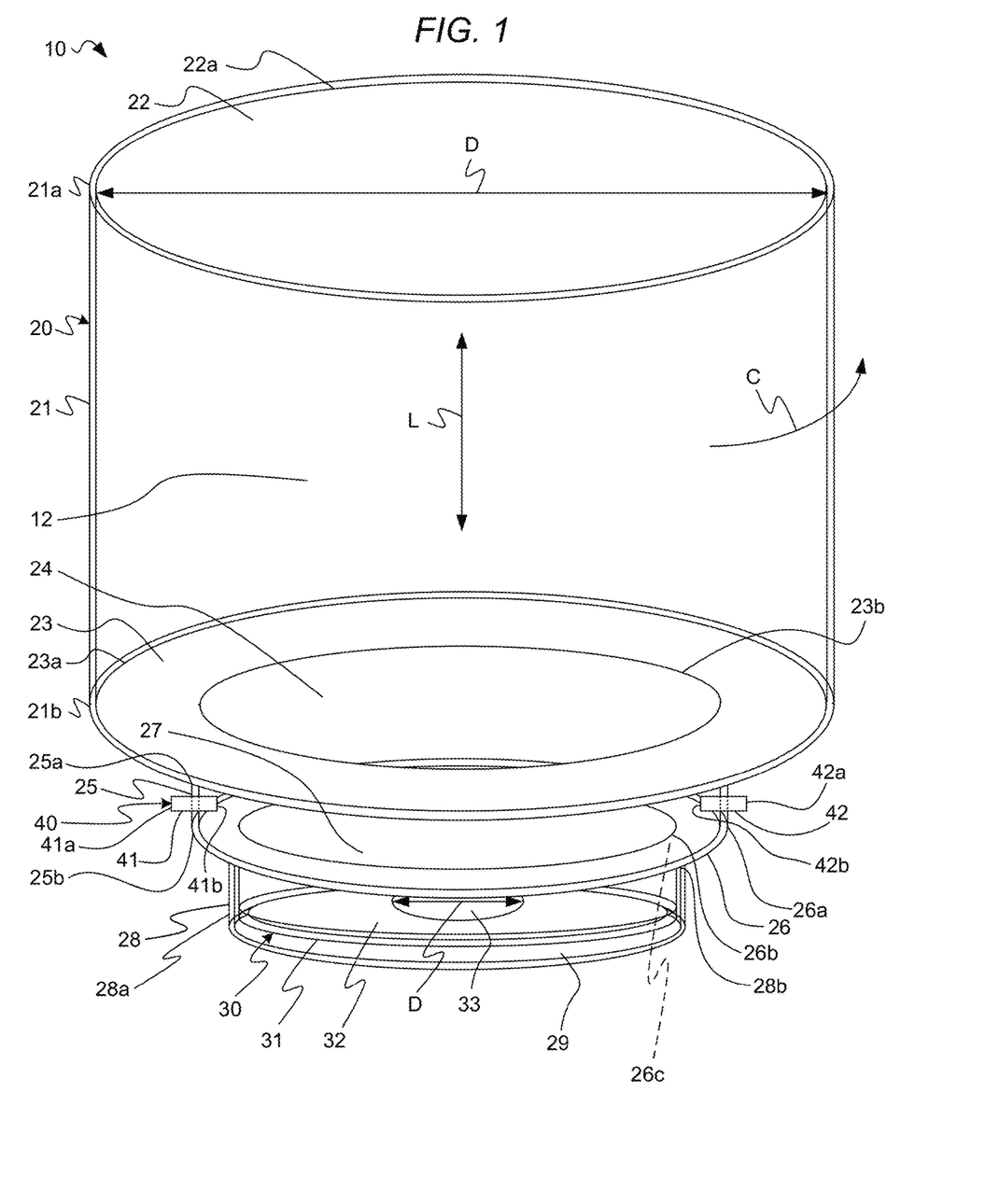
FIG. 1 is a perspective view of an isolation hood according to an embodiment of the invention.

FIG. 1 illustrates an isolation hood 10 for respiratory treatment, according to an embodiment of the invention. The isolation hood 10 may include a head enclosure 20, a neck seal assembly 30 coupled to the head enclosure, and connection ports 40 extending through the head enclosure. The isolation hood 10 may define an interior volume 12 therein configured to receive the head of a patient therein.

The head enclosure 20 is configured to extend around the head of a user with as little excess space as possible, while still having sufficient room to install a mask or nasal cannula onto a user's head for treatments such as albuterol nebulizer medication treatments, bilevel positive airway pressure (Bi-PAP) non-invasive ventilation, continuous positive pressure airway pressure (CPAP) non-invasive ventilation, nasal cannula treatment, or high flow nasal cannula treatment. The head enclosure 20 may be be connected to an oxygen source and/or ventilator to provide a positive pressure oxygen environment to assist with oxygenation. Accordingly, the diameter D of the head enclosure 20 may be between about 14 inches (35.6 cm) and about 20 inches (50.8 cm), or between about 16 inches (40.6 cm) and about 18 inches (45.7 cm). For these purposes, it is preferable that the space between the patient's mouth and nose and the nearest wall of the head enclosure 20 should be between about 2 inches (5.1 cm) and about 8 inches (20.3 cm), or between about 4 inches (10.2 cm) and about 6 inches (15.2 cm).

The head enclosure 20 serves as a barrier surface that is configured to prevent aerosolized viral or bacterial particles from flowing from the interior volume to an ambient environment outside of the head enclosure. One some examples, the head enclosure 20 may not prevent every aerosolized viral or bacterial particle from flowing to the ambient environment, but the head enclosure may prevent almost all or enough aerosolized viral or bacterial particles from flowing to the ambient environment to meet the safety needs of the treatment facility. For example, the head enclosure 20 may be equally effective at preventing aerosolized viral or bacterial particles as a negative pressure room. The head enclosure 20 may have a peripheral surface 21 extending in a circumferential direction C about a longitudinal axis L. The peripheral surface 21 may be transparent or translucent to visible light, such that a user may see through the peripheral surface while wearing the isolation hood 10. In some embodiments, the peripheral surface 21 may be partially opaque, such that a first part of the peripheral surface translucent or transparent (e.g., in front of a user's eyes) and a second part of the peripheral surface may be opaque (e.g., behind the user's head), so that the user may see through only the first part of the peripheral surface.

In one example, the peripheral surface 21 may be made of a clear vinyl or PVC sheet formed into a cylinder shape, or a portion of a clear vinyl or PVC cylindrical tube. In one example (which will be described below with reference to FIG. 4), the peripheral surface 21 may have the shape of a cylinder that is flattened on one side, such as the side adjacent to the back of a user's head. The peripheral surface 21 may be relatively stiff and hold its shape, or it may be flexible and/or easily temporarily deformable due to grasping by a user. Depending on the specific requirements needed, the peripheral surface 21 may have any thickness that is sufficient to hold a negative pressure differential of about 7.5 pascals, 15 pascals, or 30 pascals relative to the environment outside of the isolation hood 10.

The head enclosure 20 may also have a top surface 22. As shown, the top surface 22 is generally planar and extends substantially perpendicular to the longitudinal axis L, although that need not be the case. As shown, an outer periphery 22a of the top surface 22 is joined to an upper circumferential edge 21a of the peripheral surface 21 using heat sealing, epoxy, or a silicone adhesive, for example. In other examples, the peripheral surface 21 and the top surface 22 maybe a continuous single member or sheet. The top surface 22 may be translucent or transparent to visible light, or the top surface may be partially or fully opaque to visible light. The top surface 22 may be made of a clear vinyl or PVC sheet, for example. The top surface 22 may be relatively stiff and hold its shape, or it may be flexible and/or easily temporarily deformable due to grasping by a user. Depending on the specific requirements needed, the top surface 22 may have any thickness that is sufficient to hold a negative pressure differential of about 7.5 pascals, 15 pascals, or 30 pascals relative to the environment outside of the isolation hood 10.

The head enclosure 20 may have an annular base member 23 extending substantially perpendicular to the longitudinal axis L. An outer periphery 23a of the base member 23 may be joined to a lower circumferential edge 21b of the peripheral surface 21 opposite from the upper circumferential edge 21a. An inner periphery 23b of the base member 23 may extend around an opening 24 configured to receive the head of a user therethrough into the interior volume 12. As shown, the longitudinal axis L may be centered within the opening 24. In other examples, the center of the opening 24 may be laterally offset from the longitudinal axis L in a direction perpendicular to the longitudinal axis. The base member 23 may be in the form of a relatively stiff plate such as a flat PVC material, or alternatively, the base member may be a thin, flexible vinyl or PVC sheet similar to the peripheral surface 21 and/or the top surface 22.

The head enclosure 20 may also have an accessory panel 25 extending in the circumferential direction C about the longitudinal axis L. An upper circumferential edge 25a of the accessory panel 25 may be joined to the inner periphery 23b of the base member 23. The accessory panel 25 may be in the form of a relatively stiff cylindrical element such as a PVC section of a tube, or alternatively, the base member may be a thin, flexible vinyl or PVC sheet similar to the peripheral surface 21 and/or the top surface 22. The accessory panel 25 is configured to receive the connection ports 40 extending therethrough for communication with the interior volume 12 of the isolation hood 10. The connection ports 40 will be further discussed below with reference to FIGS. 2A and 2B.

The head enclosure 20 may have an annular contact surface 26 extending substantially perpendicular to the longitudinal axis L. An outer periphery 26a of the contact surface 26 may be joined to a lower circumferential edge 25b of the accessory panel 25. An inner periphery 26b of the contact surface 26 may extend around an opening 27 configured to receive the head of a user therethrough into the interior volume 12. As shown, the longitudinal axis L may be centered within the opening 27. In other examples, the center of the opening 27 may be laterally offset from the longitudinal axis L in a direction perpendicular to the longitudinal axis. The contact surface 26 may be in the form of a relatively stiff plate such as a flat PVC material, or alternatively, the contact surface may be a thin, flexible vinyl or PVC sheet similar to the peripheral surface and/or the top surface 22.

The head enclosure 20 may have a lower socket 28 defining a recess 29 therein. The lower socket 28 may have a peripheral surface 28a extending in the circumferential direction C about the longitudinal axis L. An upper circumferential edge 28b of the peripheral surface 28a may be joined to the contact surface 26 near the inner periphery 26b. The inner periphery 26b of the contact surface 26 may be closer to the longitudinal axis L than the upper circumferential edge 28b of the peripheral surface 28a, such that an inner portion 26c of the contact surface is exposed within the recess 29.

The neck seal assembly 30 may be removably coupled to the head enclosure 20 via insertion into the recess 29 of the lower socket 28. An O-ring extending around the periphery of the neck seal assembly 30 may create a virtually airtight seal between the neck assembly and the lower socket 28 of the head enclosure. The neck seal assembly 30 may have an annular housing 31 coupled to a flexible septum 32 disposed within a central opening of the annular housing. The flexible septum 32 is replaceable and removable from the neck seal assembly 30 and may be made of durable material in order to avoid tearing and to allow for easy replacement if soiled.

The flexible septum 32 may have a neck aperture 33 extending therethrough. As shown, the neck aperture 33 may centered about the longitudinal axis L of the head enclosure 20. In other examples (not shown), the neck aperture 33 may be laterally offset from the longitudinal axis L of the head enclosure 20 in a direction perpendicular to the longitudinal axis. The annular housing 31 may be affixed to the flexible septum 32, or the annular housing may be removably coupled to the flexible septum, such that the flexible septum may be removed from the annular housing and replaced. The annular housing 31 may be in the form of a relatively stiff plate such as a flat PVC material, for example. An example embodiment of the annular housing 31 that permits removable coupling of the flexible septum 32 thereto will now be described below.

Figure 2A:
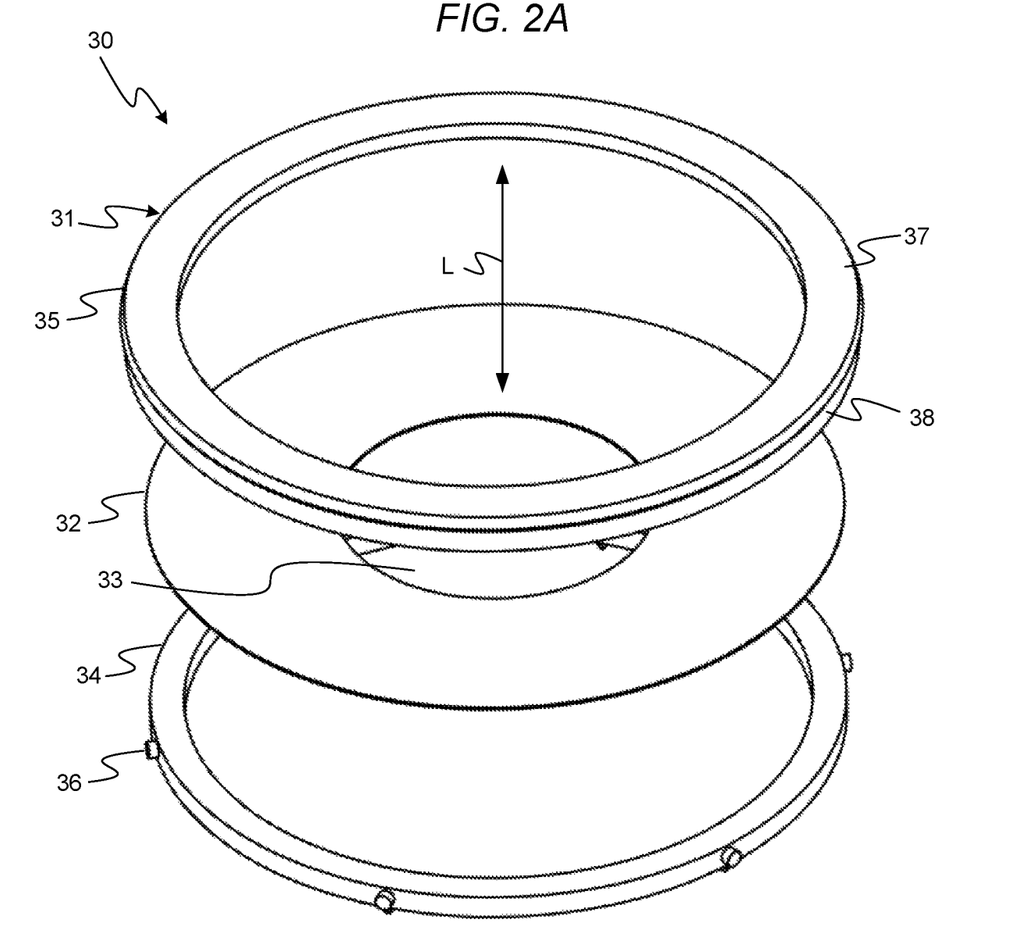
FIG. 2A is an exploded perspective view of the neck seal assembly of FIG. 1.
Figure 2B:
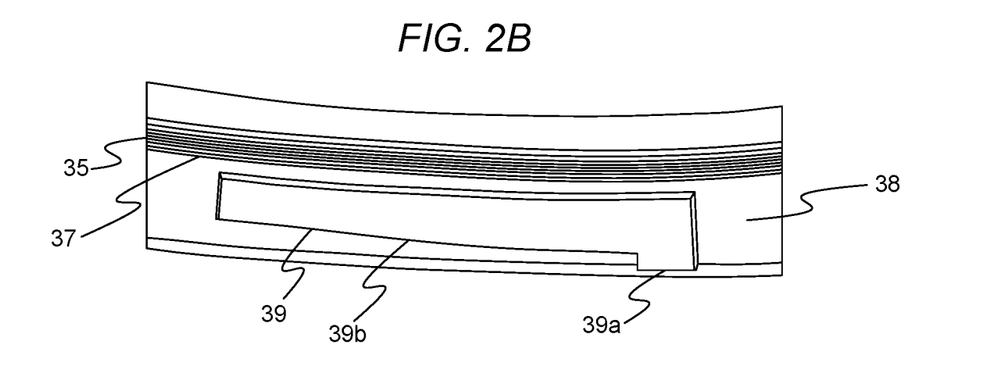
FIG. 2B is an enlarged side view of a coupling slot of the neck seal assembly of FIG. 1.

Referring to FIGS. 2A and 2B, the flexible septum 32 may be generally planar and may extend substantially perpendicular to the longitudinal axis L when the neck of a patient is not disposed within the neck aperture 33. The flexible septum 32 may be made of a flexible material such as rubber, silicone, or the like, such that when the head of a patient is pushed through the neck aperture 33, the neck aperture may stretch to accommodate the head of the patient therethrough without tearing of the flexible septum. As shown in the figures, the flexible septum 32 is generally planar, but in other embodiments, the flexible septum may have the general shape of a cylinder, a section of a cone, a section of a hyperboloid of revolution, or the like.

The flexible septum 32 may be customized to have the neck aperture 33 configured to fit a patient with a particular head diameter and/or neck diameter, such that a plurality of different flexible septa having neck apertures with different respective diameters may be provided with a single head enclosure 20. The diameter of the neck aperture 33 may be, for example, about 5 cm, about 8 cm, about 10 cm, about 12 cm, about 15 cm, or any other diameter that is configured to seal against the neck of a patient. The outer diameter of the flexible septum 32 may be various sizes, including, for example, about 20 cm to about 30 cm, or about 24 cm to about 26 cm.

The annular housing 31 may include a lower ring 34 and an upper ring 35 that together are configured to clamp the flexible septum 32 therebetween. The lower ring 34 may have a plurality of protuberances 36 extending radially outward from an outer circumferential surface of the lower ring. The protuberances 36 may be distributed about the outer circumferential surface of the lower ring 34 in a regularly spaced-apart manner. For example, the lower ring 34 may have six protuberances 36 that are spaced apart from one another about the circumferential surface by 60°.

The upper ring 35 may comprise a lateral member 37 and a vertical member 38 extending downward from the lateral member parallel to the longitudinal axis L. The vertical member 38 may have a plurality of slots 39 extending radially inward from an inner circumferential surface of the vertical member. Each slot 39 may have an opening 39a and an inclined surface 39b that gradually slopes upward towards the lateral member 37. The slots 39 may be distributed about the inner circumferential surface of the vertical member 38 in a regularly spaced-apart manner. For example, the upper ring 35 may have six slots 39 that have openings 39a that are spaced apart from one another about the circumferential surface of the vertical member 38 by 60°. The annular housing 31 preferably should have the same number of corresponding protuberances 36 and slots 39.

In order for the lower ring 34 to clamp the flexible septum 32 against the upper ring 35, a user may place the flexible septum onto an upper surface of the lower ring, and the user may raise the lower ring towards the upper ring until the protuberances 36 enter respective ones of the openings 39a. Then, the user may rotate the lower ring 34 relative to the upper ring 35, thereby sliding the protuberances 36 along the respective inclined surfaces 39b. As the protuberances 36 slide along the inclined surfaces 39b, the lower ring 34 is progressively pressed against the lateral member 37, thereby clamping the flexible septum 32 between the lower ring and the lateral member with a progressively increasing force. Once the user can no longer rotate the lower ring 34 relative to the upper ring 35, the clamping of the flexible septum 32 is complete, and the annular housing 31 may then be inserted into the recess 29 of the lower socket 28.

Although the neck seal 30 has been described having a flexible septum 32 configured to provide a seal against the neck of a patient, other variations of the flexible septum may be used. In one embodiment, the flexible septum 32 may be replaced with a neck seal having a hook and loop closure configured to fasten the neck seal around the neck of the patient.

Referring again to FIG. 1, the connection ports 40 may each extend through the accessory panel 25 of the head enclosure 20. The connection ports 40 may include one or more inlet ports 41 and one or more outlet ports 42. Although only one inlet port 41 and one outlet port 42 are shown, any number of inlet and outlet ports may be used, and the number of inlet ports need not equal the number of outlet ports. An outer end 41a of the inlet port 41 outside the head enclosure 20 may be configured to be coupled to a distal end of a standard-sized treatment source tube for treatments such as albuterol nebulizer medication treatments, bilevel positive airway pressure (BiPAP) non-invasive ventilation, continuous positive pressure airway pressure (CPAP) non-invasive ventilation, nasal cannula treatment, and/or high flow nasal cannula treatment. In one exemplary embodiment, a first inlet port 41 may be coupled to a non-invasive aerosol-generating treatment, while a second inlet port 41 may be coupled to an input of one or more of air, gas, or oxygen. In this example, this configuration would permit the first inlet port 41 to be used for a nebulizer, while the second inlet port 41 may be used to supply medical air or oxygen to allow 50 liters/minute of flow to flush out carbon dioxide that the patient is exhaling. In one example, the outer end 41a of one of the inlet ports 41 may be configured to provide a gas flow to washout excess $CO_2$ from the interior volume 12 of the isolation hood 10. The gas flow may be provided at a flow rate that is sufficient to prevent hypercarbia.

An inner end 41b of the inlet port 41 inside the head enclosure 20 may be configured to be coupled to a first end of a treatment delivery tube. The treatment delivery tube may have various inner diameters depending on the treatment used, and the inner diameter may range between about 15 mm and about 19 mm. The end of the treatment delivery tube may have a larger diameter for fitting onto the inner end of the connection ports 40, such as between about 18 mm and about 22 mm. The inner end and the outer end of the connection ports 40 may have outer diameters between about 18 mm and about 22 mm, and the outer diameter of the connection ports should correspond to the inner diameter of the end of the treatment delivery tube and/or inline particle filter, so that a virtually airtight seal is created therebetween.

An outer end 42a of the outlet port 42 outside of the head enclosure 20 may be configured to be coupled to an inline particle filter (e.g., a viral/bacterial filter). The inline particle filter may be configured to permit air to flow from the interior volume 12 through the head enclosure 20 to the outside. The inline particle filter may be configured to prevent the aerosolized viral or bacterial particles from flowing from the interior volume 12 to the ambient environment outside of the head enclosure 20. Depending on the desired treatment, an inner end 42b of the outlet port 42 may be configured to be coupled to an outflow tube from the mask or nasal cannula worn by the user.

As shown in the figures, the connection ports 40 are each shown oriented perpendicular to the longitudinal axis L and extending through the accessory panel 25. In other examples, the connection ports 40 may have other orientations with respect to the longitudinal axis L and may extend through the contact surface 26 and/or the base member 23. In one example, each of the connection ports 40 may extend through the contact surface 26 and oriented parallel to the longitudinal axis L. In some embodiments, one or more of the connection ports 40 may have an inner end 41b, 42b that is oriented parallel to the longitudinal axis L and an outer end 41a, 42a that is oriented perpendicular to the longitudinal axis, such that the connection ports may be elbow-shaped. In some examples (not shown), the connection ports 40 may include an access port, which may be a small port extending through the accessory panel 25, the contact surface 26, or the base member 23, through which a straw may be passed through to allow patient to drink.

As shown, the connection ports 40 are un-threaded and un-tapped, such that a treatment tube or inline particle filter may be press-fit onto the inner end and/or the outer end of the connection ports. In other examples, one end or both ends of one or more of the connection ports 40 may be threaded and/or tapped, such that a treatment tube or inline particle filter may be screwed or rotated onto the inner end and/or the outer end via a conventional screw thread, a luer lock, or the like. In some embodiments, the connection between the connection ports 40 and the treatment tube or inline particle filter may be removably pushed onto one another in a snap-fit manner, using a protrusion/recess or ring/groove interaction that may be uncoupled if a sufficient pulling force is applied to overcome the snap-fit.

In one example, the connection ports 40 may include a pressure port, an outer end of the pressure port outside the head enclosure 20 configured to be coupled to a distal end of a suction tube, the suction tube configured to remove gas from the interior volume 12 within the head enclosure to maintain the interior volume below atmospheric pressure. In another example, the connection ports 40 may include a pressure port, an outer end of the pressure port outside the head enclosure 20 configured to be coupled to a distal end of a high-pressure tube, the high-pressure tube configured to supply a pressurized gas into the interior volume 12 within the head enclosure to maintain the interior volume above atmospheric pressure. In some examples, the pressure port may be used with an inline positive end expiratory pressure valve coupled thereto.

Figure 2C:
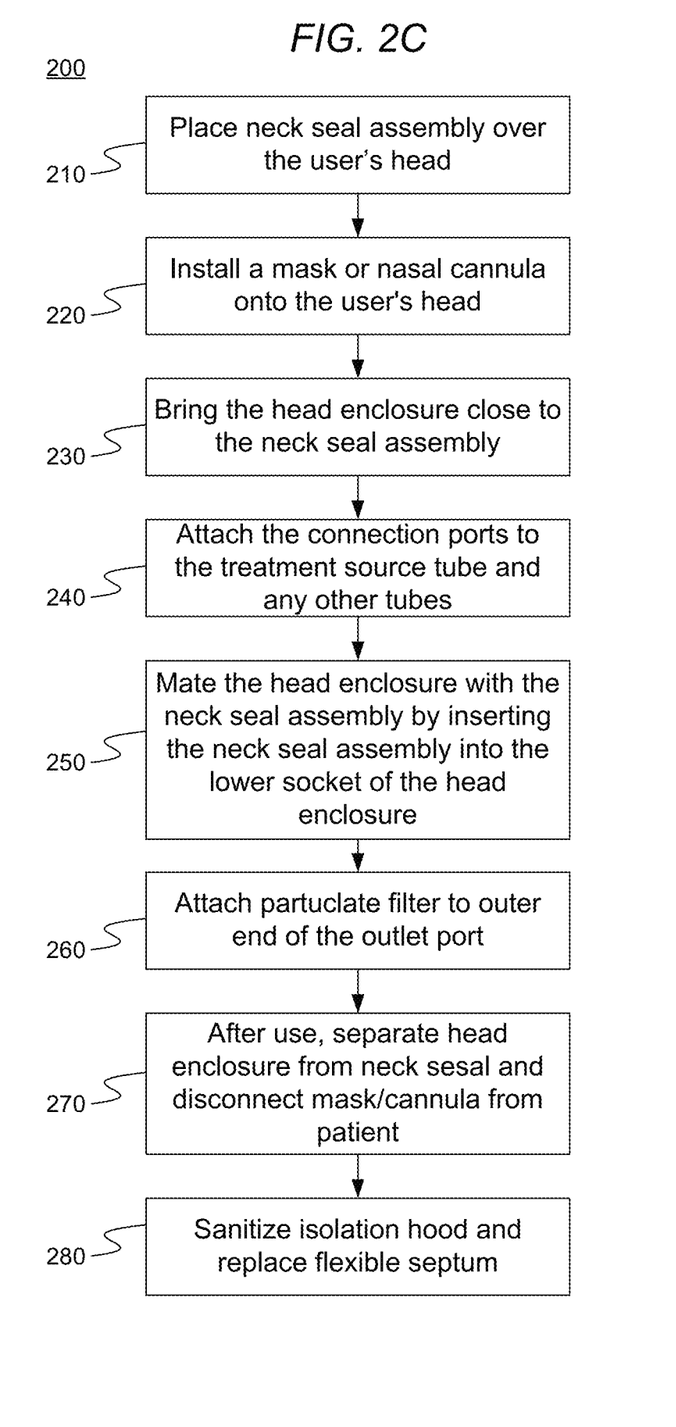
FIG. 2C is a flow chart displaying a method of using the isolation hood FIG. 1.

Referring now to FIG. 2C, a method 200 of using the isolation hood 10 of FIGS. 1 through 2B will now be described. First, at step 210, based on the size of a user's neck and/or head, a corresponding-sized neck seal assembly 30 is placed over the user's head, such that the neck aperture 33 creates a seal against the user's neck. Then, at step 220, a physician installs a mask or nasal cannula onto a user's head for treatments such as albuterol nebulizer medication treatments, bilevel positive airway pressure (BiPAP) non-invasive ventilation, continuous positive pressure airway pressure (CPAP) non-invasive ventilation, nasal cannula treatment, or high flow nasal cannula treatment.

Next, at step 230, once the mask or nasal cannula is properly installed, the head enclosure 20 is brought close to the neck seal assembly 30, and at step 240, the physician attaches the connection ports 40 (one or more inlet ports 41 and one or more outlet ports 42) to the treatment source tube and/or any outlet tube that extends from the mask or cannula to an outlet port. Then, at step 250, the head enclosure 20 is mated with the neck seal assembly 30 by placing the neck seal assembly into the lower socket 28. An O-ring extending around the periphery of the neck seal assembly 30 may create a virtually airtight seal between the neck assembly and the lower socket 28 of the head enclosure. At step 260, either before or after the mating of the head enclosure 20 with the neck seal assembly 30, a particulate filter may be installed onto the outer end 42a of the outlet port 42.

At step 270, to remove the isolation hood 10 from the patient, the physician may pull the head enclosure 20 off of the neck seal assembly 30, but the head enclosure should remain close enough to the neck seal assembly to disconnect the treatment source tube and/or any outlet tube from the connection ports 40. Then, at step 280, the head enclosure 20 may be sterilized and re-used for the same user or a different user. The neck seal assembly 30 may be disassembled so that a new flexible septum 32 may be installed between the lower ring 34 and the upper ring 35.

Figure 3:
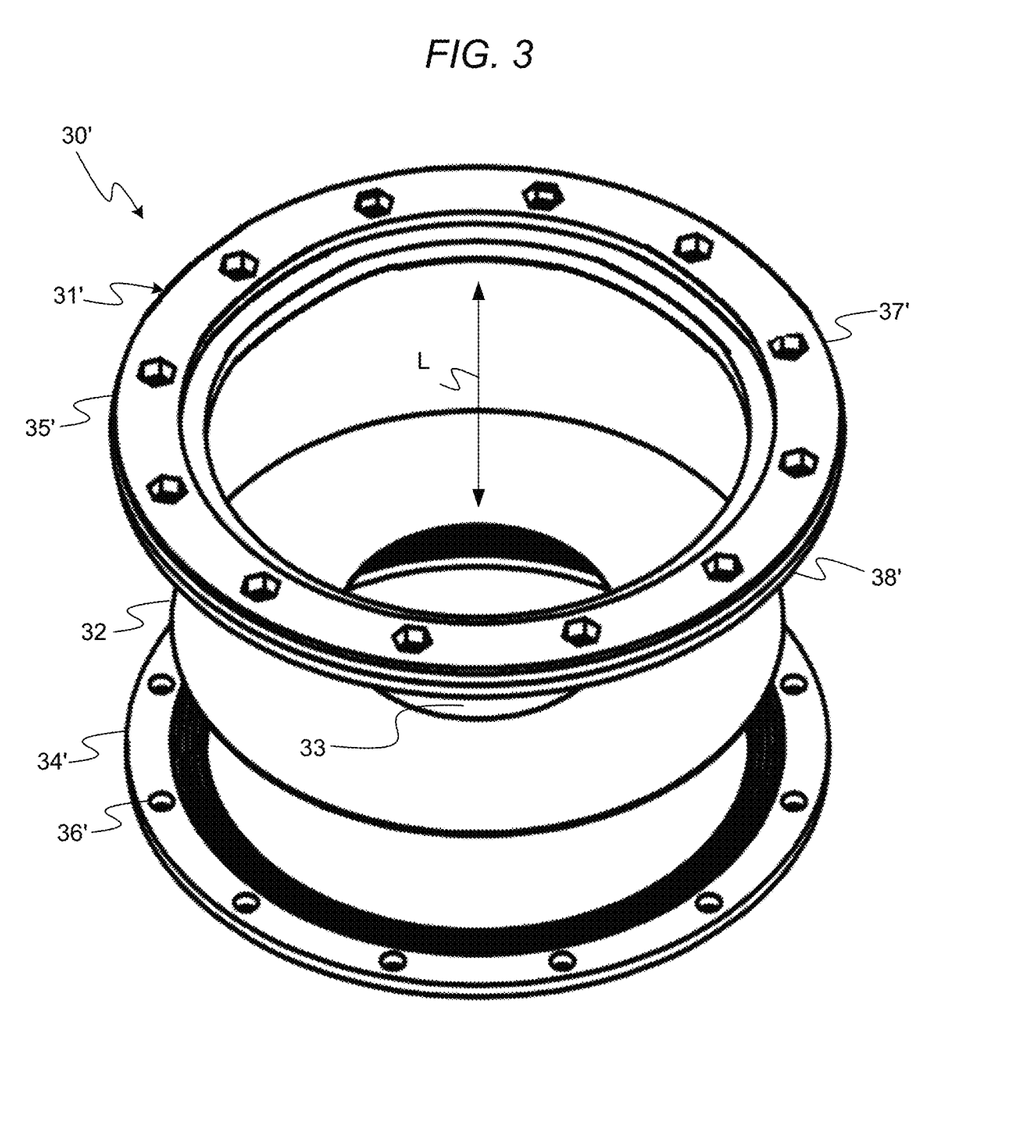
FIG. 3 is an exploded perspective view of a neck seal assembly according to another embodiment of the invention that is a variation of the neck seal assembly of FIGS. 2A and 2B.

Referring now to FIG. 3, a neck seal assembly 30' according to an alternative embodiment may be removably coupled to the head enclosure 20 in place of the neck seal assembly 30 of FIGS. 1, 2A, and 2B. Similar to the neck seal assembly 30, the neck seal assembly 30' may have an annular housing 31' coupled to a flexible septum 32 disposed within a central opening of the annular housing, which may be the same flexible septum described above, or which may be any one of the variations of the flexible septum that are described above.

The annular housing 31' may include a lower ring 34' and an upper ring 35' that together are configured to clamp the flexible septum 32 therebetween. The lower ring 34' and the upper ring 35' may each have a plurality of apertures 36' extending through the respective ring in a vertical direction parallel to the longitudinal axis L. The apertures 36' may be distributed about the outer circumferential surface of the lower ring 34' and the upper ring 35' in a regularly spaced-apart manner. For example, each ring 34', 35' may have twelve apertures 36' that are spaced apart from one another about the circumferential surface by 30°. The annular housing 31' preferably should have the same number of corresponding apertures 36' in each of the lower ring 34' and the upper ring 35'. The upper ring 35' may comprise a lateral member 37' and a vertical member 38' extending downward from the lateral member parallel to the longitudinal axis L.

In order for the lower ring 34' to clamp the flexible septum 32 against the upper ring 35', a user may place the flexible septum onto an upper surface of the lower ring, and the user may raise the lower ring towards the upper ring until the apertures 36' of the lower ring and the upper ring are circumferentially aligned. Then, the user may fasten the lower ring 34' to the upper ring 35', sliding bolts into the corresponding apertures 36' and tightening the bolts by threading nuts thereon. As the bolts are tightened, the lower ring 34' is progressively pressed against the lateral member 37', thereby clamping the flexible septum 32 between the lower ring and the lateral member with a progressively increasing force. Once the bolts are sufficiently tightened, the clamping of the flexible septum 32 is complete, and the annular housing 31' may then be inserted into the recess 29 of the lower socket 28.

Figure 4:
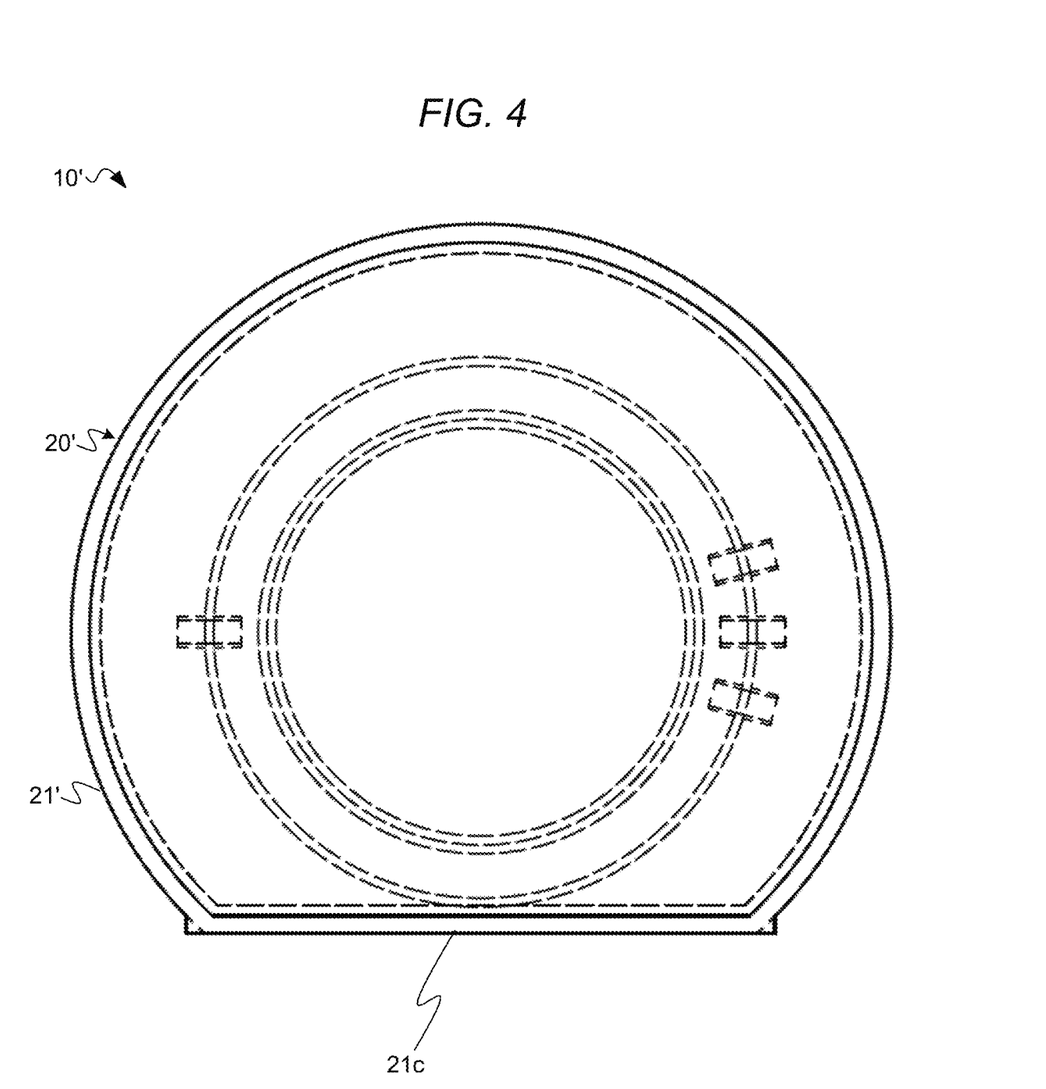
FIG. 4 is a top plan view of a head enclosure according to another embodiment of the invention that is a variation of the head enclosure of FIG. 1.

Referring now to FIG. 4, an isolation hood 10' having a head enclosure 20' having a flattened rear portion according to an alternative embodiment may be used in place of the neck head enclosure 20' of FIGS. 1, 2A, and 2B. Similar to the head enclosure 20, head enclosure 20' may have a peripheral surface 21' that may extend around the head of a user. However, rather than having a fully-cylindrical shape, the head enclosure 20' has a peripheral surface 21' with a flattened rear portion 21c. In one example, the flattened rear portion 21c may be opaque, while the remainder of the peripheral surface 21' is translucent or transparent. The flattened rear portion 21c of the isolation hood 10' may make it easier for a user to recline his or her head against a pillow compared to the isolation hood 10, considering that the back of the user's head may be much closer to the flattened rear portion than the remainder of the peripheral surface 21'.

Figure 5:
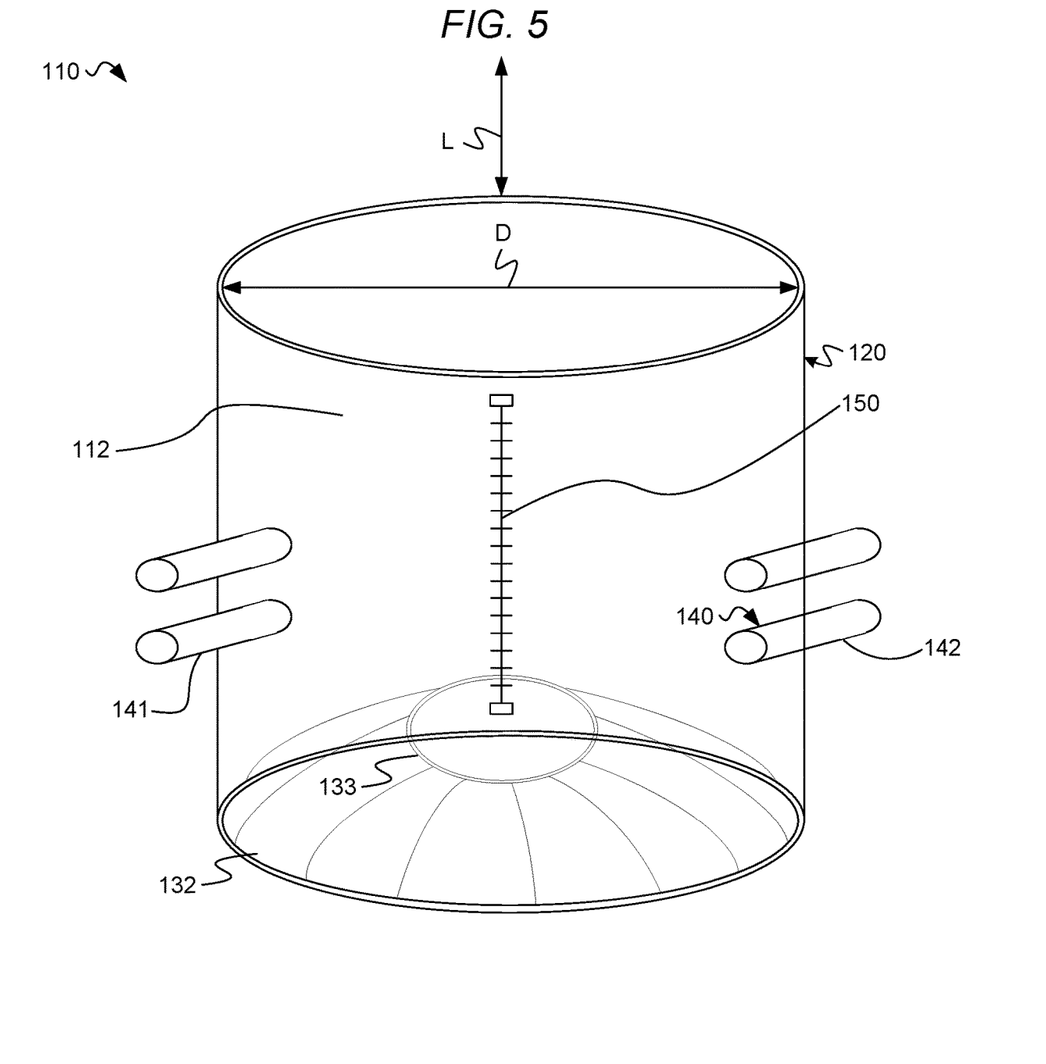
FIG. 5 is a perspective view of an isolation hood according to another embodiment of the invention that is a variation of the head isolation hood of FIG. 1.

Referring now to FIG. 5, an isolation hood 110 that is a variation of the isolation hood 10 has a head enclosure 120 with a flexible septum 132 that is affixed to the head enclosure, such that the head enclosure and the flexible septum are an integrated unit surrounding the interior volume 112 and are not intended to be separated from one another. The flexible septum 132 comprises the entire neck assembly, rather than having a separate neck assembly that is assembled with the head enclosure 120 once the neck assembly is already placed around the neck of a user.

The isolation hood 110 has a zipper 150 that permits a physician to insert his or her hands into the interior volume 112 within the head enclosure 120, in order to place a mask or nasal cannula onto a user's head for treatments such as albuterol nebulizer medication treatments, bilevel positive airway pressure (BiPAP) non-invasive ventilation, continuous positive pressure airway pressure (CPAP) non-invasive ventilation, nasal cannula treatment, or high flow nasal cannula treatment. The physician can also attach the connection ports 140 (one or more inlet ports 141 and one or more outlet ports 142) to the treatment source tube and/or any outlet tube that extends from the mask or cannula to an outlet port. The head enclosure 120 may be made of a translucent or transparent vinyl or PVC, for example, while the flexible septum 132 may be made of a silicone sheet having a neck aperture 133 extending therethrough, for example.

Although the examples disclosed herein have been described with reference to specific embodiments, it is to be appreciated that these embodiments are merely illustrative examples of the potential structures and uses of the present invention. The invention contemplates that numerous modifications may be made to the examples described and that other configurations may be included within the scope of the present invention without departing from the spirit of the invention as defined by the appended claims. It should be understood that various dependent claims of the application and the features recited therein can be combined in different ways besides those presented in the initial claims. It should also be understood that particular features described with reference to any of the examples disclosed herein may be shared with any other examples found elsewhere in the disclosure.

The invention claimed is:

1. An isolation hood for respiratory treatment, the isolation hood comprising:
a head enclosure defining an interior volume therein and configured to receive the head of a patient within the interior volume, the head enclosure having an opening at a bottom thereof, the opening configured to receive the neck of the patient therein, the head enclosure having a diameter between 35 cm and 51 cm, the head enclosure configured to have a space between the mouth and nose of the patient and a nearest wall of the head enclosure between 5 cm and 20 cm;
a neck seal disposed at the opening, the neck seal configured to couple the head enclosure to the neck of the patient, the neck seal configured to prevent aerosolized viral or bacterial particles from flowing from the interior volume to an ambient environment outside of the head enclosure;
an inlet port extending through the head enclosure, an outer end of the inlet port outside the head enclosure configured to be coupled to a distal end of a treatment source tube, an inner end of the inlet port inside the head enclosure coupled to a first end of a treatment delivery tube of a non-invasive aerosol-generating treatment placed on the head of the patient, while a second end of the treatment delivery tube coupled to the head of the patient; and
an outlet port extending through the head enclosure, an outer end of the outlet port outside of the head enclosure configured to be coupled to an inline particle filter, the inline particle filter configured to prevent the aerosolized viral or bacterial particles from flowing from the interior volume to the ambient environment outside of the head enclosure,
the inlet port configured to connect to the non-invasive aerosol-generating treatment within the interior volume, the non-invasive aerosol-generating treatment including: bilevel positive airway pressure ventilation, continuous positive airway pressure ventilation, nebulizer treatments, oxygen cannula, mask, or high-flow nasal cannula treatments to the patient.

2. The isolation hood of claim 1, wherein the inlet port is a first inlet port, the isolation hood further comprising a second inlet port extending through the head enclosure and configured to be coupled to the non-invasive aerosol-generating treatment or an input of one or more of air, gas, or oxygen.

3. The isolation hood of claim 1, wherein the neck seal comprises a neck ring that is configured to be removably coupled to an inner edge of the head enclosure at the opening, the neck seal having an outer periphery attached to the neck ring and an inner aperture remote from the outer periphery.

4. The isolation hood of claim 1, further comprising the inline particle filter coupled to the outer end of the outlet port.

5. The isolation hood of claim 4, further comprising an inline positive end expiratory pressure valve coupled to the inline particle filter or the outer end of the outlet port and configured to maintain the interior volume above atmospheric pressure.

6. The isolation hood of claim 1, wherein the neck seal comprises a hook and loop closure configured to fasten the neck seal around the neck of the patient.

7. The isolation hood of claim 1, further comprising a pressure port, an outer end of the pressure port outside the head enclosure configured to be coupled to a distal end of a suction tube, the suction tube configured to remove gas from the interior volume within the head enclosure to maintain the interior volume below atmospheric pressure.

8. The isolation hood of claim 7, further comprising a viral filter in line with the suction tube.

9. The isolation hood of claim 1, further comprising a pressure port and an inline positive end expiratory pressure valve, an outer end of the pressure port outside the head enclosure configured to be coupled to a distal end of a high-pressure tube, the high-pressure tube configured to supply a pressurized gas into the interior volume within the head enclosure to maintain the interior volume above atmospheric pressure, the inline positive end expiratory pressure valve coupled to the pressure port or the outer end of the outlet port and configured to maintain the interior volume above atmospheric pressure.

10. The isolation hood of claim 1, further comprising the mask, wherein the mask is a nebulizer treatment mask.

11. The isolation hood of claim 1, further comprising the mask, wherein the mask is a continuous positive airway pressure system mask or a bilevel positive airway pressure system mask.

12. The isolation hood of claim 1, further comprising the nasal cannula, wherein the nasal cannula is a high flow nasal cannula.

13. The isolation hood of claim 1, wherein the inlet port is configured to provide a gas flow to washout excess $CO_2$ from the interior volume of the isolation hood, the gas flow being provided at a flow rate that is sufficient to prevent hypercarbia.

14. A kit comprising the isolation hood of claim 1 and an alternate neck seal, wherein the neck seal and the alternate neck seal have inner apertures having different diameters, the neck seal and the alternate neck seal each configured to be removably coupled to an inner edge of the head enclosure at the opening.

15. A method of using an isolation hood for respiratory treatment, the method comprising:
  placing a neck seal around a neck of a patient;
  after the placing of the neck seal, coupling a first end of a treatment delivery tube to a head of the patient;
  after the coupling of the first end of the treatment delivery tube, placing a head enclosure around a head and neck of a patient, the head enclosure defining an interior volume in which the head of the patient is received;
  after the placing of the head enclosure, coupling the head enclosure to the neck seal, the head enclosure having an opening at a bottom thereof extending around the neck of the patient, an inner edge of the opening being coupled to a peripheral edge of the neck seal, the isolation hood having an inlet port and an outlet port each extending through the head enclosure, an outer end of the inlet port coupled to a distal end of a treatment source tube, an outer end of the outlet port coupled to an inline particle filter, an inner end of the inlet port coupled to a second end of the treatment delivery tube; and
  flowing a medicine in a carrier gas or another aerosol-generating treatment through the treatment source tube and through the treatment delivery tube, wherein the neck seal and the inline particle filter together prevent the aerosolized viral or bacterial particles from flowing from the interior volume to the ambient environment outside of the head enclosure.

16. The method of claim 15, further comprising suctioning gas out of the interior volume through a pressure port extending through the head enclosure, the suctioning maintaining the interior volume below atmospheric pressure.

17. The method of claim 15, further comprising flowing a pressurized gas into the interior volume through a pressure port extending through the head enclosure, the pressurized gas maintaining the interior volume above atmospheric pressure using at least one of: a pressure valve or a positive end expiratory pressure valve inline on the outlet port.

18. The method of claim 15, wherein the second end of the treatment delivery tube comprises a nebulizer treatment mask, and the medicine is a nebulizer treatment compound.

19. The method of claim 15, wherein the second end of the treatment delivery tube comprises a continuous positive airway pressure system mask, a bilevel positive airway pressure system mask, or a nasal cannula.

* * * * *